United States Patent [19]
Kallok et al.

[11] Patent Number: 5,215,082
[45] Date of Patent: Jun. 1, 1993

[54] IMPLANTABLE APNEA GENERATOR WITH RAMP ON GENERATOR

[75] Inventors: Michael J. Kallok, New Brighton; H. Toby Markowitz, Roseville, both of Minn.

[73] Assignee: Medtronic, Inc., Minneapolis, Minn.

[21] Appl. No.: 679,120

[22] Filed: Apr. 2, 1991

[51] Int. Cl.⁵ .............................................. A61N 1/08
[52] U.S. Cl. ................................................. 128/419 G
[58] Field of Search ................................... 128/419 G

[56] References Cited

U.S. PATENT DOCUMENTS

| | | | |
|---|---|---|---|
| 4,506,666 | 3/1985 | Durkan | 128/419 G |
| 4,570,631 | 2/1986 | Durkan | 128/419 G |
| 4,827,935 | 5/1989 | Geddes et al. | 128/419 G |
| 4,830,008 | 5/1989 | Meer | 128/421 |

FOREIGN PATENT DOCUMENTS 0404427 12/1990 European Pat. Off.

OTHER PUBLICATIONS

Glenn, William W. L., Diaphragm Pacing: Present Status, 1977.
Cook, William R., & Osguthorpe, J. David, Obstructive Sleep Apnea: Diagnosis and Treatment, Dec. 1985.

Primary Examiner—Kyle L. Howell
Assistant Examiner—Scott M. Getzow
Attorney, Agent, or Firm—Harold R. Patton; Daniel W. Latham; John L. Rooney

[57] ABSTRACT

An implantable system for the treatment of obstructive sleep apnea by electrical stimulation of the musculature of the upper airway. The system employs one or more sensors to determine the onset of an apnea event. Upon sensing of the onset of an apnea event, the stimulation generator provides a signal for stimulating the muscles of the upper airway at a varying intensity wherein the intensity is gradually increased during the course of the stimulation. The signal is coupled to the muscles to be stimulated by an electrode connected to the stimulation generator by an insulated lead.

5 Claims, 5 Drawing Sheets

IMPLANTABLE APNEA GENERATOR WITH RAMP ON GENERATOR

CROSS REFERENCE TO CO-PENDING APPLICATIONS

U.S. patent application Ser. No. 07/610,854, filed Nov. 8, 1990, entitled "Muscle Tone"; U.S. patent application Ser. No. 07/617,158, filed Nov. 23, 1990, entitled "Multiple Stimulation Electrodes;" U.S. patent application Ser. No. 07/639,192, filed Jan. 9, 1991, entitled "Servo Muscle Control"; and U.S. patent application Ser. No. 671,513, filed Mar. 19, 1991, entitled "Demand Apnea Control", are all assigned to the assignee of the present invention and incorporated herein by reference.

BACKGROUND OF THE INVENTION

1. Field of the Invention

The present invention relates generally to implantable medical devices, and more particularly, relates to implantable medical devices for the treatment of obstructive sleep apnea.

2. Description of the Prior Art

The medical characteristics of sleep apnea have been known for some time. There are two generally recognized forms of the disease. The first is central sleep apnea which is associated with the failure of the body to automatically generate the neuro-muscular stimulation necessary to initiate and control a respiratory cycle at the proper time. Work associated with employing electrical stimulation to treat this condition is discussed in "Diaphragm Pacing: Present Status", by William W. L. Glenn, in Pace, Volume I, at pages 357-370 (July-September 1978).

The second condition is known as obstructive sleep apnea. It is discussed at some length in "Obstructive Sleep Apnea: Diagnosis and Treatment", by Drs. Cook and Osguthorpe in *Journal of South Carolina Medical Association*, 81 (12): 647-651 (December 1985).

At present, a tracheostomy may be the treatment of choice for a number of patients when obstructive sleep apnea is severe. Some modern commercial systems now employ Continuous Positive Airway Pressure (CPAP). However, interest has recently been displayed in electrical stimulation of the muscle tissue along the upper airway during respiration. U.S. Pat. No. 4,830,008 issued to Meer discusses a technique for electrical stimulation of the muscles of the upper airway in synchrony with the respiratory cycle. U.S. Pat. No. 4,506,666 issued to Durkan discusses such stimulation in conjunction with pressurized airflow supplied by a respirator.

The electrical stimulation of the prior art techniques, however, are primarily concerned with causing contractile motion of the stimulated muscle. This means that the stimulation energy must necessarily be relatively large, and the effects of the stimulation are directly cognizable by the patient.

SUMMARY OF THE INVENTION

The present invention overcomes the deficiencies of the prior art by providing a system for treatment of obstructive sleep apnea having a minimum cognizable effect upon the patient. This is particularly important as the purpose of the therapy is to preclude disturbing the patient to ensure that the maximum benefit from sleep is derived.

The system employs at least one sensor to monitor the respiration activity. In this way, the implantable pulse generator can determine the onset of an apnea event from indications within the respiratory cycle of the patient. In the preferred mode, the pressure differential between the thorax and the upper airway is measured. An increase in this differential above a given threshold signifies the onset of an apnea event.

To treat the apnea event, the implantable pulse generator produces a train of pulses which is transferred to the muscles of the upper airway via an insulated lead and a suitable electrode. The train of pulses is initiated at a relatively low intensity with the pulse intensity increasing over time. In this manner, the patient is provided with a non-cognizable sensation produced by the stimulation signal.

Since effective skeletal muscle stimulation depends upon both the amplitude and frequency of the stimulation pulses, a suitable frequency must be employed. By slowly increasing amplitude, the patient's sensory response to the stimulii exhibits adaptation, a well known phenomenon, that permits the brain to effectively block the pain response to noxious stimulii.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
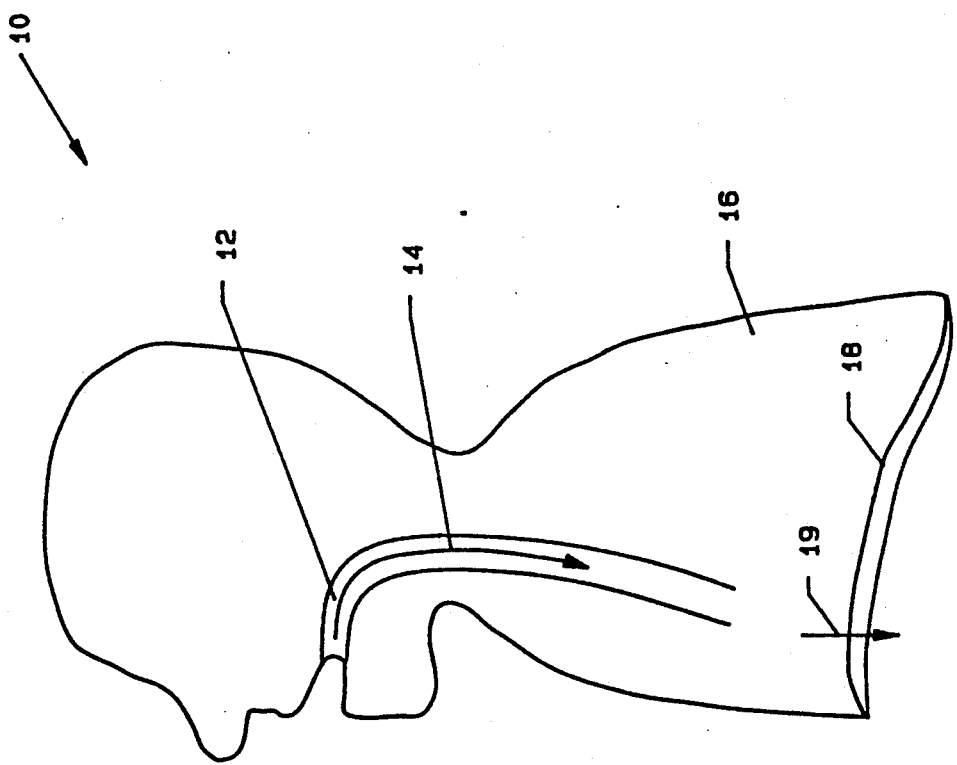
FIG. 1 is a schematic diagram of the respiratory system of a patient.

FIG. 1 is a schematic diagram of the respiratory system of patient 10 during inspiration. As a result of the contraction of diaphragm 18 moving in the direction of arrow 19, the volume of thorax 16 is increased. A partial vacuum is created causing air to enter upper airway 12 and proceed in the direction of arrow 14.

Figure 2:
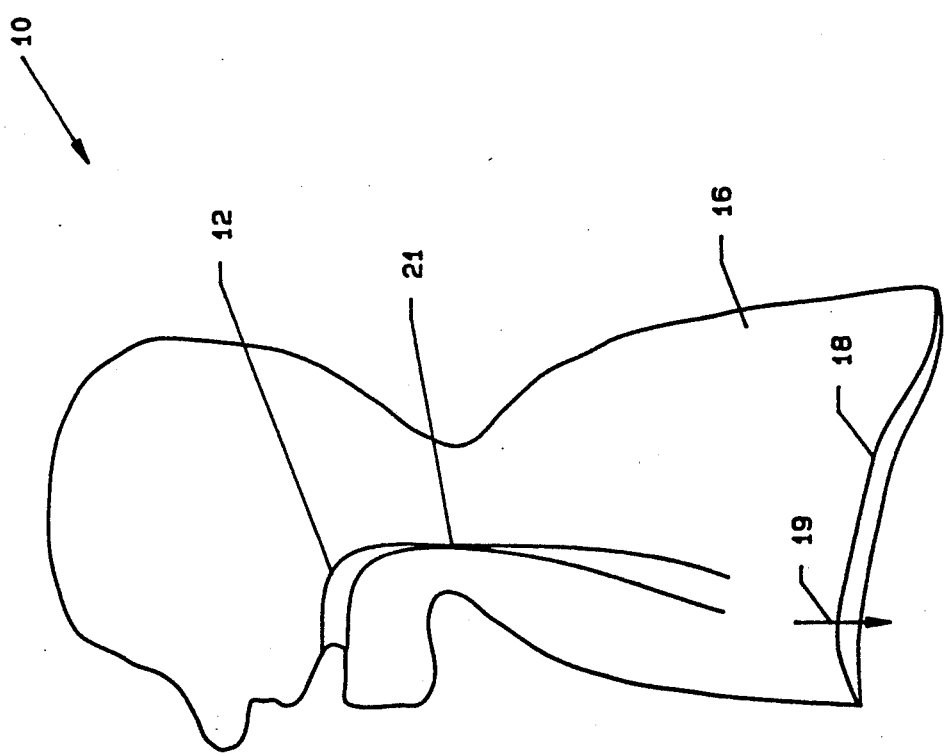
FIG. 2 is a schematic diagram of the respiratory system showing an obstructive apnea event.

FIG. 2 is a schematic diagram of the respiratory system of patient 10 during an obstructive apnea event. During inspiration, upper airway 12 tends to collapse producing the obstruction to air flow at point 21. The above referenced literature describes in detail the physiological processes associated with the collapse of upper airway 12.

Figure 3:
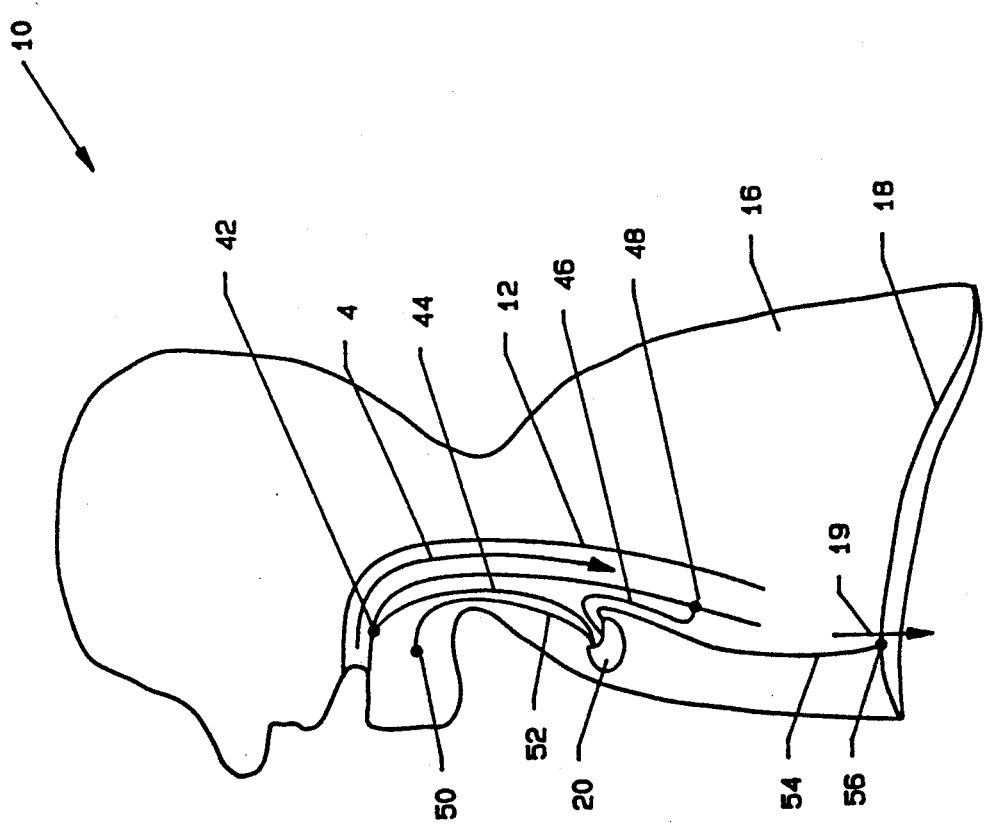
FIG. 3 is a schematic diagram of the respiratory system of a patient having an obstructive apnea treatment system implanted.

FIG. 3 is a schematic diagram of patient 10 showing implantation of an electrical stimulation system for the treatment of both central and obstructive sleep apnea. Implantable pulse generator 20 is placed subcutaneously at a convenient position. Diaphragm 18 is electrically monitored via electrode 56 coupled to lead 54. This provides the means to synchronize any stimulation supplied to the inspiration cycle.

Patency of upper airway 12 is monitored by pressure sensor 42 and pressure sensor 48 coupled to implantable pulse generator 20 via cables 44 and 46, respectively. Stimulation of the musculature of upper airway 12 is accomplished via lead 52 coupled to electrode 50. All other referenced elements are as previously described.

Figure 4:
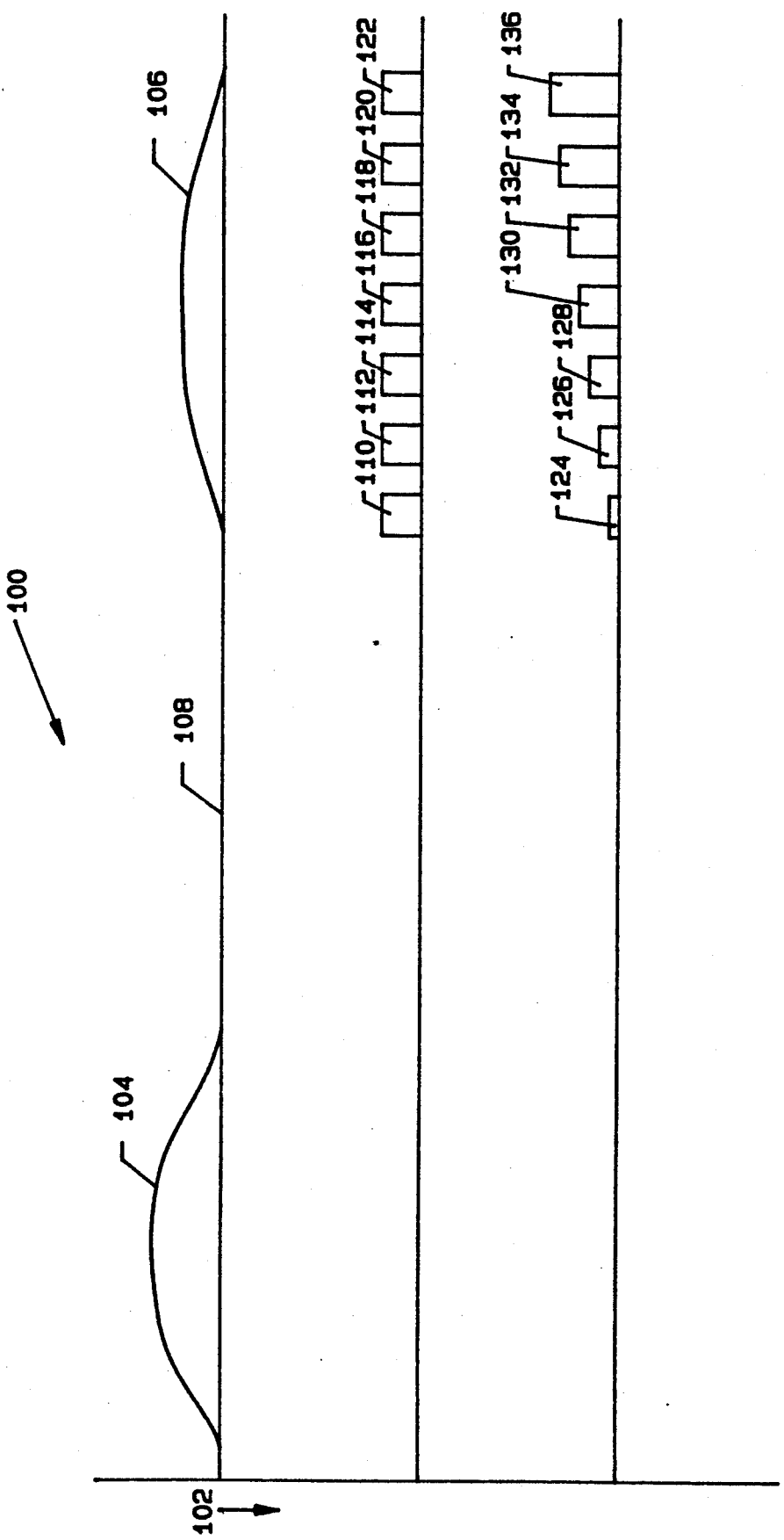
FIG. 4 is a graphical representation of the sensor input and implantable pulse generator output of the obstructive apnea treatment system; and, FIG. 5 is a block diagram of an implantable pulse generator according to the present invention.

FIG. 4 is a graphical representation 100 of the inputs and outputs of implantable pulse generator 20. Graph 108 represents the pressure differential between the upper airway and the thorax as measured between pressure sensor 42 and pressure sensor 48 wherein a decrease of pressure is shown by arrow 102. Node 104 shows a high pressure difference during inspiration which is indicative of an obstructive apnea event. Node 106 shows a much smaller differential as a result of stimulation of the musculature of the upper airway.

The second graph shows a train of stimulation pulses, including pulses 110, 112, 114, 116, 118, 120, and 122, according to the prior art stimulation technique. Note that each of the pulses is of the same relatively high intensity. This stimulation tends to result in arousal of patient 10 from sleep.

The bottom line shows a train of stimulation pulses generated in accordance with the present invention. First pulse 124 is of minimum intensity. Pulses 126 through 136 are gradually increased in amplitude until maximum intensity is reached with pulse 136. Note that by ramping from low to high intensity it is possible to reach a higher amplitude with less sensation to the patient than is possible with constant intensity stimulation. This permits a more effective contraction with less sensation due to the phenomenon of adaptation. It might also permit one to vary the frequency of stimulation (i.e. reduce frequency) to save energy and prolong the life of the pulse generator.

Figure 5:
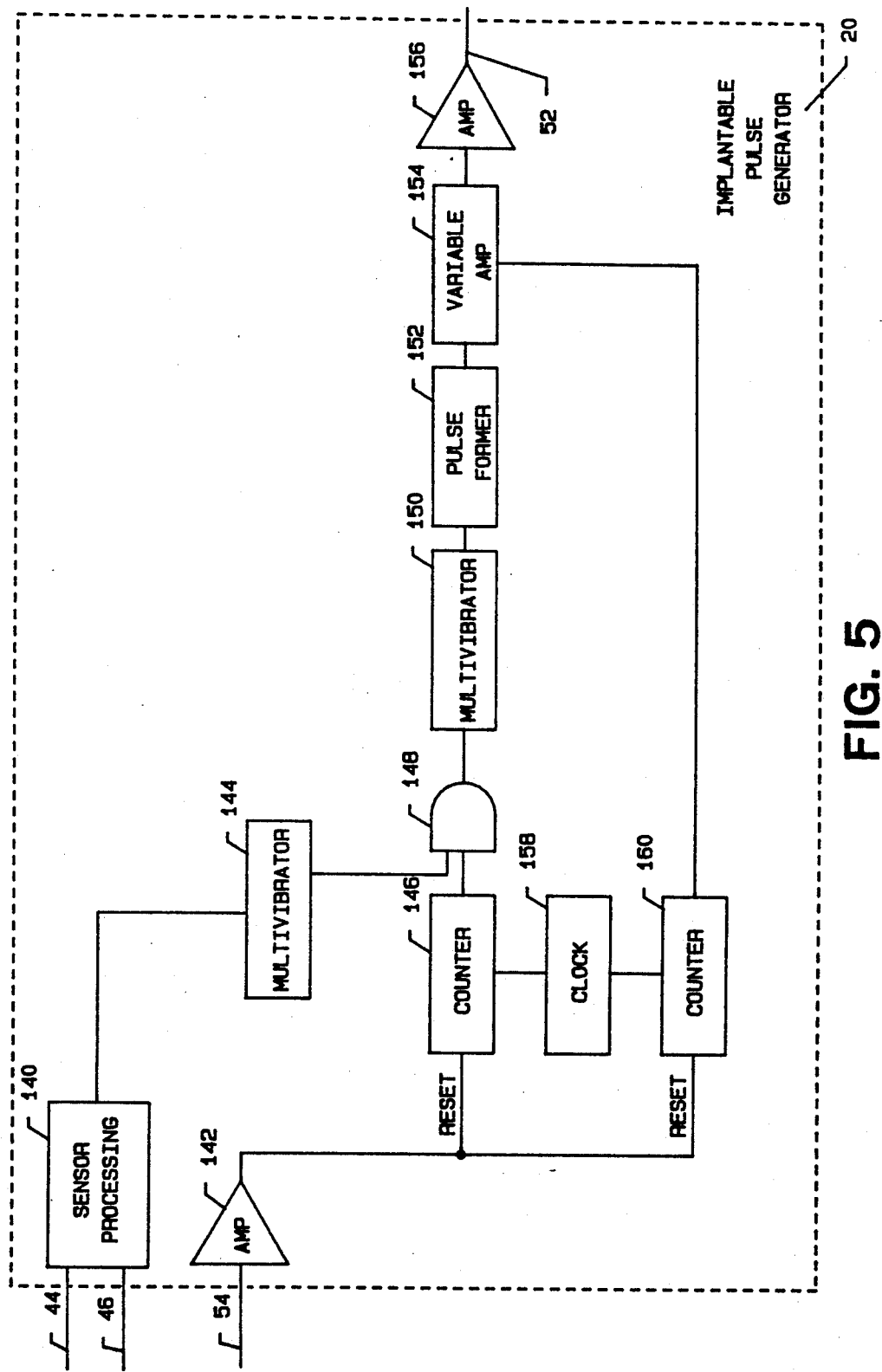

FIG. 5 is a block diagram of implantable pulse generator 20. Sensor processing 140 determines the pressure differential between the upper airway and the thorax by comparing the measurements received from pressure sensors 42 and 48 via cables 44 and 46, respectively. Whenever this difference exceeds a given threshold, an output pulse is supplied to multi-vibrator 144 for pulse shaping.

Each inspiration cycle may be electrically monitored by electrode 56 coupled to lead 54 (see also FIG. 3). The signal is amplified by amplifier 142 and used to reset counter 146 and counter 160. Counter 146 is driven by clock 158 and is used to delay generation of the stimulation pulse train to synchronize it with the inspiration cycle. And gate 148 provides an output whenever multi-vibrator 144 indicates an obstruction is Multi-vibrator 150 shapes the pulse to initiate the stimulation pulse train. Pulse former 152 provides the proper number of pulses with the desired pulse width.

Counter 160 as reset by amplifier 142 controls the gain of variable amplifier 154. In this way, the amplification of the individual pulses output by pulse former 152 is varied to produce the variable intensity output according to the present invention (see also FIG. 4). Amplifier 156 has a fixed gain and supplies the output to lead 52 for transmission to electrode 50 (see also FIG. 3).

Having thus described the preferred embodiments of the present invention, those of skill in the art will be readily able to apply the teachings found herein to yet other embodiments within the scope of the claims hereto attached.

We claim:

1. An apparatus comprising:
    a. means for determining the onset of an apnea event comprising means for measuring a pressure differential between the thorax and the upper airway;
    b. means coupled to said determining means for generating a stimulation signal in response to said onset of said apnea event; and,
    c. means coupled to said generating means for varying the amplitude of said stimulation signal from a minimum intensity to a maximum intensity.

2. An apparatus according to claim 1 further comprising means coupled to said generating means for synchronizing said stimulation signal with an inspiration cycle.

3. An apparatus according to claim 2 wherein said varying means produces said minimum intensity at a beginning of said stimulation signal.

4. An apparatus according to claim 3 wherein said measuring means comprises a first pressure sensor located in said thorax and a second pressure sensor located in said upper airway.

5. An apparatus according to claim 4 wherein said synchronizing means comprises an electrode for sensing contraction of the diaphragm.

* * * * *

UNITED STATES PATENT AND TRADEMARK OFFICE
CERTIFICATE OF CORRECTION

PATENT NO. : 5,215,082
DATED : June 1, 1993
INVENTOR(S) : Michael J. Kallok and H. Toby Markowitz It is certified that error appears in the above-indentified patent and that said Letters Patent is hereby corrected as shown below:

```
Column 4, line 5, after "is" please insert --present as
      synchronized by counter 146.--
```

Signed and Sealed this

Fourteenth Day of June, 1994

Attest:

BRUCE LEHMAN

Attesting Officer                Commissioner of Patents and Trademarks